US011802859B2

(12) United States Patent
Su et al.

(10) Patent No.: US 11,802,859 B2
(45) Date of Patent: Oct. 31, 2023

(54) WIRELESS SELF-POWERED GAS SENSOR BASED ON ELECTROMAGNETIC OSCILLATIONS TRIGGERED BY EXTERNAL FORCES AND FABRICATION METHOD THEREOF

(71) Applicant: University of Electronic Science and Technology of China, Chengdu (CN)

(72) Inventors: Yuanjie Su, Chengdu (CN); Qichen Gong, Chengdu (CN); Yanmeng Chen, Chengdu (CN); Guangzhong Xie, Chengdu (CN); Huiling Tai, Chengdu (CN); Xiaosong Du, Chengdu (CN); Yadong Jiang, Chengdu (CN)

(73) Assignee: UNIVERSITY OF ELECTRONIC SCIENCE AND TECHNOLOGY OF CHINA, Chengdu (CN)

( * ) Notice: Subject to any disclaimer, the term of this patent is extended or adjusted under 35 U.S.C. 154(b) by 417 days.

(21) Appl. No.: 17/120,239

(22) Filed: Dec. 13, 2020

(65) Prior Publication Data

US 2021/0208121 A1      Jul. 8, 2021

(30) Foreign Application Priority Data

Dec. 12, 2019   (CN) .......................... 201911273836.8
Dec. 12, 2019   (CN) .......................... 201911274569.6

(51) Int. Cl.
    *G01N 33/00*    (2006.01)
    *G01N 27/12*    (2006.01)
    *H02N 1/04*    (2006.01)

(52) U.S. Cl.
    CPC ......... *G01N 33/0059* (2013.01); *G01N 27/12* (2013.01); *G01N 27/122* (2013.01);
(Continued)

(58) Field of Classification Search
    CPC .. G01N 27/12; G01N 27/125; G01N 33/0027; G01N 33/0047; G01N 27/128; G01N 33/0009; H02N 1/04
See application file for complete search history.

(56) References Cited

U.S. PATENT DOCUMENTS

2021/0320596 A1* 10/2021 Su ........................... H02N 1/04

FOREIGN PATENT DOCUMENTS

CN    106018498 A * 10/2016 ............. G01N 27/12
CN    106525910 A *  3/2017 ........... G01N 27/048
(Continued)

*Primary Examiner* — Benjamin R Schmitt
(74) *Attorney, Agent, or Firm* — MATTHIAS SCHOLL P.C.; Matthias Scholl (57) ABSTRACT

The disclosure relates to a wireless self-powered gas sensor based on electromagnetic oscillations triggered by external forces and its fabrication method. The sensor includes a gas test chamber, a first friction layer, a second friction layer, an interdigital electrode, a gas-sensitive material, an air inlet, an air outlet and leads. The gas sensor of the disclosure is an integrated detection system of "environmental energy collection—wireless energy transmission—active spontaneous detection" that can be driven simultaneously only by external mechanical movement, and can work independently without external power supply. The first friction layer and the second friction layer are arranged outside the gas test chamber. The frictional motion will not interfere with the flow field of the test chamber and the gas molecule absorption and desorption, which ensures the stability of gas detection to the greatest extent.

8 Claims, 8 Drawing Sheets

(52) U.S. Cl.
CPC ....... *G01N 27/125* (2013.01); *G01N 33/0027* (2013.01); *G01N 33/0031* (2013.01); *G01N 33/0047* (2013.01); *H02N 1/04* (2013.01); *G01N 27/128* (2013.01); *G01N 33/0009* (2013.01)

(56) References Cited

FOREIGN PATENT DOCUMENTS

| | | | | | |
|---|---|---|---|---|---|
| CN | 109540997 | A | * | 3/2019 | ......... G01N 27/4071 |
| CN | 109540998 | A | * | 3/2019 | ......... G01N 27/4071 |

* cited by examiner

WIRELESS SELF-POWERED GAS SENSOR BASED ON ELECTROMAGNETIC OSCILLATIONS TRIGGERED BY EXTERNAL FORCES AND FABRICATION METHOD THEREOF

CROSS-REFERENCE TO RELAYED APPLICATIONS

Pursuant to 35 U.S.C. § 119 and the Paris Convention Treaty, this application claims foreign priority to Chinese Patent Application No. 201911274569.6 filed on Dec. 12, 2019, and to Chinese Patent Application No. 201911273836.8 filed on Dec. 12, 2019. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND

The disclosure relates to a wireless self-powered gas sensor based on electromagnetic oscillations triggered by external forces and fabrication method thereof.

At present, all sensors developed and produced are powered by battery or wired power transmission, which requires regular battery replacement and power grid maintenance to ensure the continuous operation of the network, which not only increases the economic cost, but also greatly reduces the mobility and environmental adaptability of sensor network nodes. Secondly, in order to detect and identify mixed VOCs gases, gas sensors are often fabricated into arrays to improve the selectivity of sensors, which leads to huge energy consumption of the whole node, and battery power alone cannot meet the long-term working requirements of such sensor nodes. The endurance of battery demands for reduced power consumption in the system. Harvesting energy from ambient environment for powering wireless sensor nodes together with energy management and energy delivery technology are conducive to long-term operation of wireless sensor network.

SUMMARY

To solve the problems of traditional gas sensors, such as short life, high power consumption and the need for external power supply, the disclosure provides with an energy acquisition and transmission mechanism and method enabled by polymer materials and polarization. Without any metal electrode and wire connection, the proposed approach simplifies device structure and integration process, further improves the compatibility of energy supplying module and sensor. In addition, the current self-driven gas sensors require external energy sources to act directly on the device, the spatial range of energy collection can only be limited to the sensor location and cannot collect environmental energy outside the device location, As a consequence, the application range and space utilization rate are dramatically hampered. The disclosure proposes the self-driven sensing mechanism and model of wireless energy transmission. This disclosure is an integrated detection system of environmental energy collection-wireless energy transmission-active detection that can be completely driven by external mechanical movement alone. Moreover, the proposed device can work independently without external power supply. The energy collected from the energy harvesting component can be wirelessly sent to the gas-sensitive sensing component, which improves the environmental applicability of the sensor.

The disclosure provides a wireless self-powered gas sensor and array based on electromagnetic oscillations triggered by external forces and related fabrication method. In the disclosure, the first friction layer and the second friction layer as the energy harvesting component, promote the sliding motion stemmed from external airflow or mechanical motion, and transform the external mechanical energy into the time-varying electric displacement field to spread outwards. The two ends of interdigital electrode wirelessly collect the energy of the time-varying electric displacement field and yield an induced current. Chemical specific reactions are modulated into electrical signals on the energy-conversion surface to realize self-driven detection of gas type and concentration.

A wireless self-powered gas sensor with electromagnetic oscillations triggered by external force comprises an energy harvesting component and a gas sensing component.

The energy harvesting component comprises a first friction layer and a second friction layer. The cross-sectional area of the friction layer is the same as that of the gas test chamber. The second friction layer is completely aligned with the outer surface of the gas test chamber. The first friction layer is located above the second friction layer. The first friction layer is grating structure and made of negative friction material, and the second friction layer is made of positive friction material. The grating is parallel to the electrode of interdigital electrodes (IDEs) with identical characteristic parameters.

The gas sensing component comprises a gas test chamber and an interdigital electrode. The interdigital electrode is located on the bottom layer of the gas test chamber, and the gaps of adjacent electrodes are filled with gas-sensitive material. The two ends of interdigital electrode are wired to detect the electrical signal of the sensor, so as to realize the self-driven detection of the type and concentration of the target gas. The opposite sides of the gas test chamber are integrated with an air inlet and an air outlet respectively for the quantitative injection and discharge of the target gas, respectively.

Figure 1A:
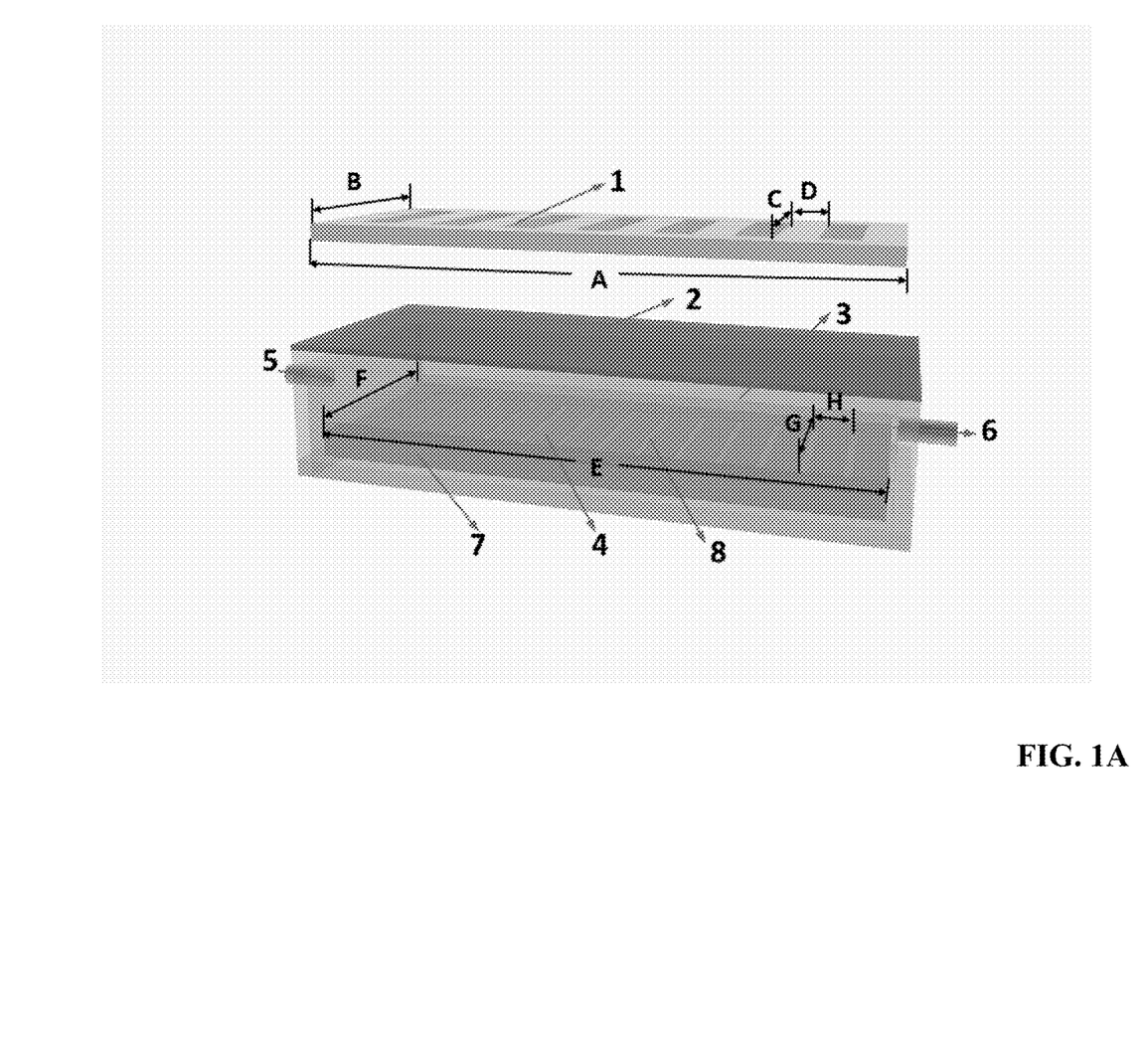
FIGS. 1A-1B illustrates the structure diagram of the wireless self-powered gas sensor based on electromagnetic oscillations triggered by external forces (FIG. 1A) and the structure diagram of the interdigital electrode (FIG. 1B)
Figure 1B:
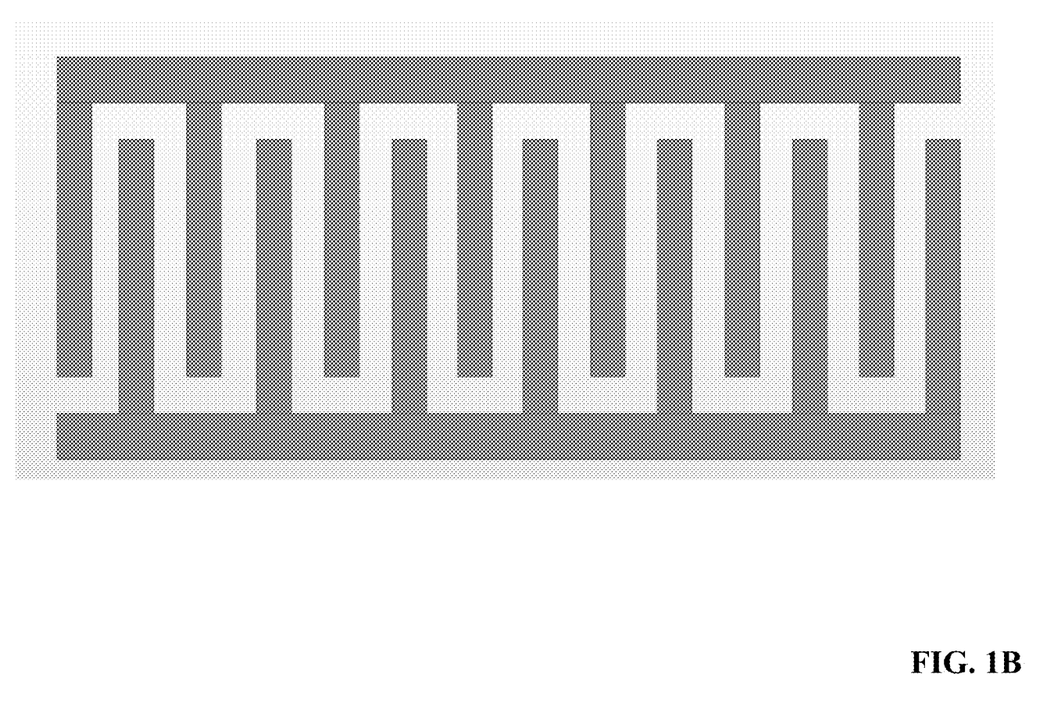

In a class of this embodiment, the grating in the first friction layer is parallel to the electrode in the interdigital electrode and the following characteristic parameters are identical for these two configurations. The length of the whole grating is A, the width of the whole grating is B, the width of the transmittance part of the grating is C in the longitudinal direction, the width of the solid part of the grating is D in the transverse direction, with a duty ratio of 0.5. The length of the entire interdigital electrode is E, the width of the entire interdigital electrode is F, the longest distance between the two adjacent interdigital electrodes is G in the direction of the width of the interdigital electrode, and the crosswise width of each comb electrode in the fork finger electrode is H. Then A=E, B=F, C=G, D=H. The solid part of grating in the first friction layer owns the same width as the interdigital electrode.

In a class of this embodiment, the gas-sensitive material is a single or composited material of organic polymer, a metal oxide and an inorganic material that is sensitive to the target gas.

In a class of this embodiment, the gas-sensitive material is composed of one or more different materials among polyaniline, polyvinyl oxide, polyimide, sodium polystyrene sulfonate, polyimide, chitosan, and graphene oxide.

In a class of this embodiment, the first friction layer is the first polymer film, and the second friction layer is the second polymer film. The first polymer film holds a stronger electron affinity the second polymer film and thus the ability to attract electrons from the second polymer film.

In a class of this embodiment, the first friction layer is made of teflon, polyfluoroethylene, polyvinyl chloride or polyimide with a thickness of 10-50 μm, the second friction layer is selected from nylon, polyurethane or magnesium fluoride and has a thickness of 10-50 μm.

The method for preparing a wireless self-powered gas sensor based on electromagnetic oscillations triggered by external forces comprises:

1) cleaning and drying two pieces of polymer films;

2) cutting a first polymer film into grating structure by laser as a first polymer film; cutting a second piece into a rectangular structure as a second polymer film; where the first polymer film and the second polymer film are utilized together as triboelectric materials; and the electron affinity ability of the first polymer film is stronger than that of the second polymer film;

3) preparing the interdigital electrode through spin coating, spray coating, drop coating, sol gel, self-assembly or chemical vapor deposition; developing a gas-sensitive structure by depositing the gas-sensitive material between the adjacent electrodes of the interdigital electrode in combination with a lift-off process;

4) using a laser cutting machine to cut a plexiglass plate and assemble the gas test chamber; attaching the second polymer film to the outer surface of the top of the gas test chamber as the second friction layer; placing the first polymer film above the second polymer film as the first friction layer; both sides of the gas test chamber are integrated air inlet and air outlet; and placing the gas-sensitive structure at the bottom of the gas test chamber to form a self-driven gas sensor; and 5) connecting the two ends of the interdigital electrode to a test port of a current measuring instrument through a lead.

Compared with the prior art, the beneficial effects of the disclosure are as follows:

Traditional self-driven gas sensors all require external energy sources to directly power the device, that is, the space range of energy collection can only be limited at the location of the sensor, and the environmental energy outside the location of the device cannot be collected, so its application range and space utilization ratio are weakened to a large extent. The disclosure provides a wireless self-powered gas sensor based on electromagnetic oscillations triggered by external forces, which is an integrated detection system of "environmental energy collection—wireless energy transmission—active spontaneous detection" that can be driven simultaneously only by external mechanical movement, and can work independently without external power supply. The first friction layer and the second friction layer are arranged outside the gas test chamber. The frictional motion will not interfere with the flow field of the test chamber and the gas molecule absorption and desorption, which ensures the stability of gas detection to the greatest extent. The energy collected from the part of energy supply can be transmitted to the gas-sensitive detection interface wirelessly, which improves the environmental applicability and individual mobility of the sensor. The sensor does not need any metal electrode and wire connection, which simplifies the device structure and integration process.

Attached figure marks: 1. First friction layer; 2. Second friction layer; 3. Gas test chamber; 4. Interdigital electrode; 5. Air inlet; 6. Air outlet; 7. Acrylic plate; 8. Gas sensitive material; 41. First interdigital electrode; 42, Second interdigital electrode; 43. Third interdigital electrode; 81. First in sensitive material; 82. Second gas sensitive material; and 83. Third gas sensitive material.

DETAILED DESCRIPTION

To further illustrate, embodiments detailing a wireless self-powered gas sensor based on electromagnetic oscillations triggered by external forces and fabrication method thereof are described below. It should be noted that the following embodiments are intended to describe and not to limit the disclosure.

EXAMPLE 1

In this implementation, the proposed device is sensitive to ammonia gas, and the first friction layer is selected from polytetrafluoroethylene (PTFE), the second friction layer is selected from Nylon material (Nylon) and the gas-sensitive material is selected from polyaniline.

The method for preparing the wireless self-powered gas sensor in Example 1 specifically includes the following steps:

Step 1. Cleaning with acetone, ethanol and deionized water for 15 min in turn and drying of polytetrafluoroethylene (PTFE) and nylon films. The thickness of the two films is 25 m and the size is 10 cm×3 cm.

Step 2. Using a laser cutting machine to cut PTFE film into a grating structure. The length and width of the whole grating are 10 cm and 3 cm respectively. The width of the transmittance part of the grating is 2 cm in the longitudinal direction, the width of the solid part of the grating is 0.5 cm in the transverse direction, and the duty cycle is 0.5.

Step 3. Preparing polyaniline mixture and forming electrode. Adding 0.488 g ammonium persulfate (APS) and 1 mL aniline to 200 mL 2 mol/L HCl, stir and mix evenly to obtain the polyaniline mixture. The substrate with an interdigital electrode was adhered by PE film, exposing only the gap between the interdigital electrodes. Immersing the interdigital electrode in the polyaniline mixture for 30 min and then removing PE film. The treated interdigital electrode can be obtained.

Step 4: Using laser cutting machine to cut four acrylic plates. The size of two acrylic plates are 10 cm×3 cm. The size of the other two acrylic plates is 3 cm×3 cm, and a round vent hole is cut in their center respectively. The size of the vent hole is 0.6 cm×0.6 cm. Then, with a two-liquid mixed hardening adhesive (AB adhesive), bonding the acrylic plates into a gas test chamber, attaching the nylon film onto the top outer surface of the gas test chamber as the second friction layer, locating the PTFE film with grating structure above the second polymer film as the first friction layer. Connecting the processed interdigital electrode to the bottom of the gas test chamber. Then, a self-driven gas sensor can be formed through the above steps.

Step 5. Connecting the two ends of the interdigital electrode to a test port of a current measuring instrument through a lead.

Figure 3:
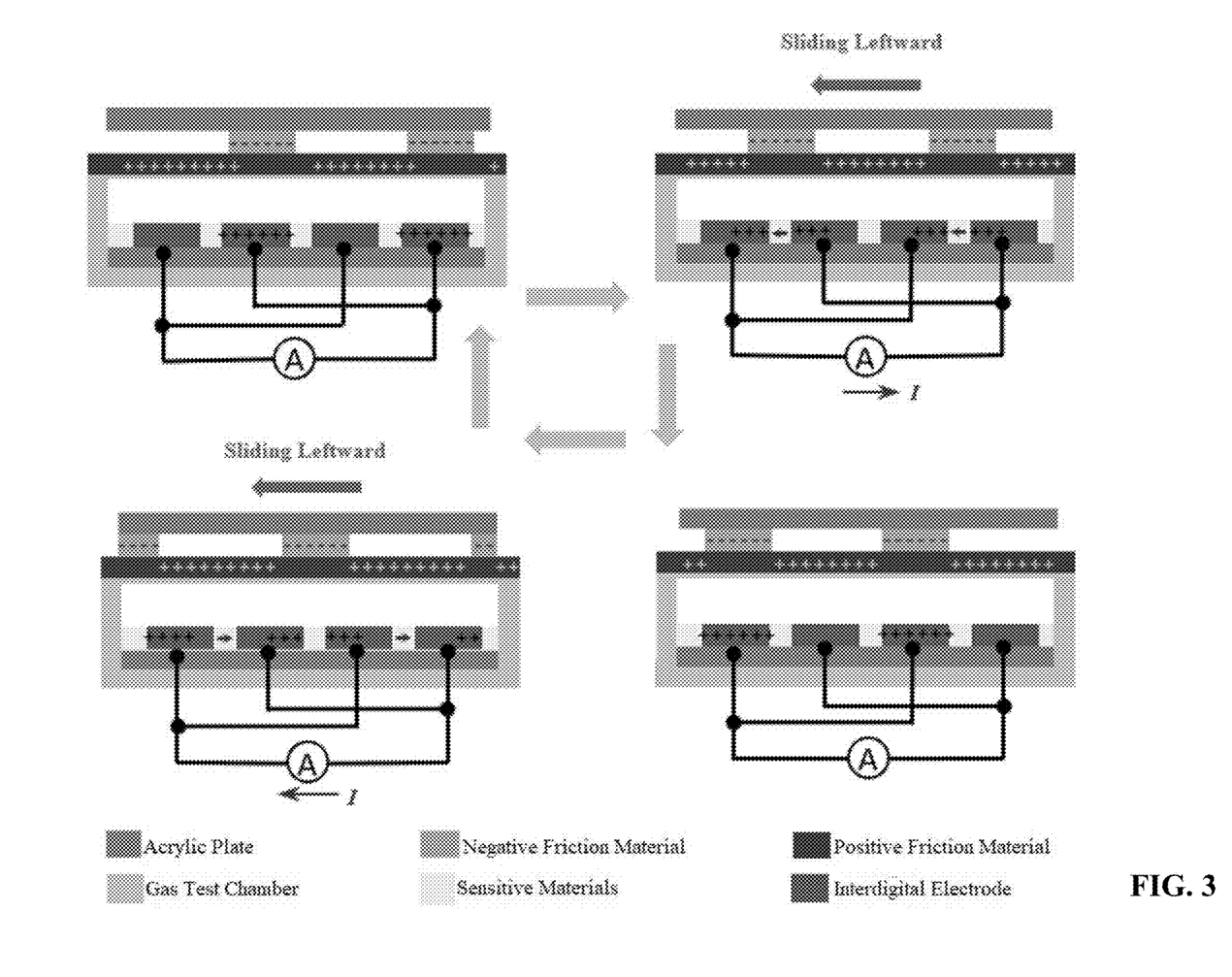
FIGS. 3 and 4 show the conductive mechanism diagram when the sliding direction of the first friction layer is different.
Figure 4:
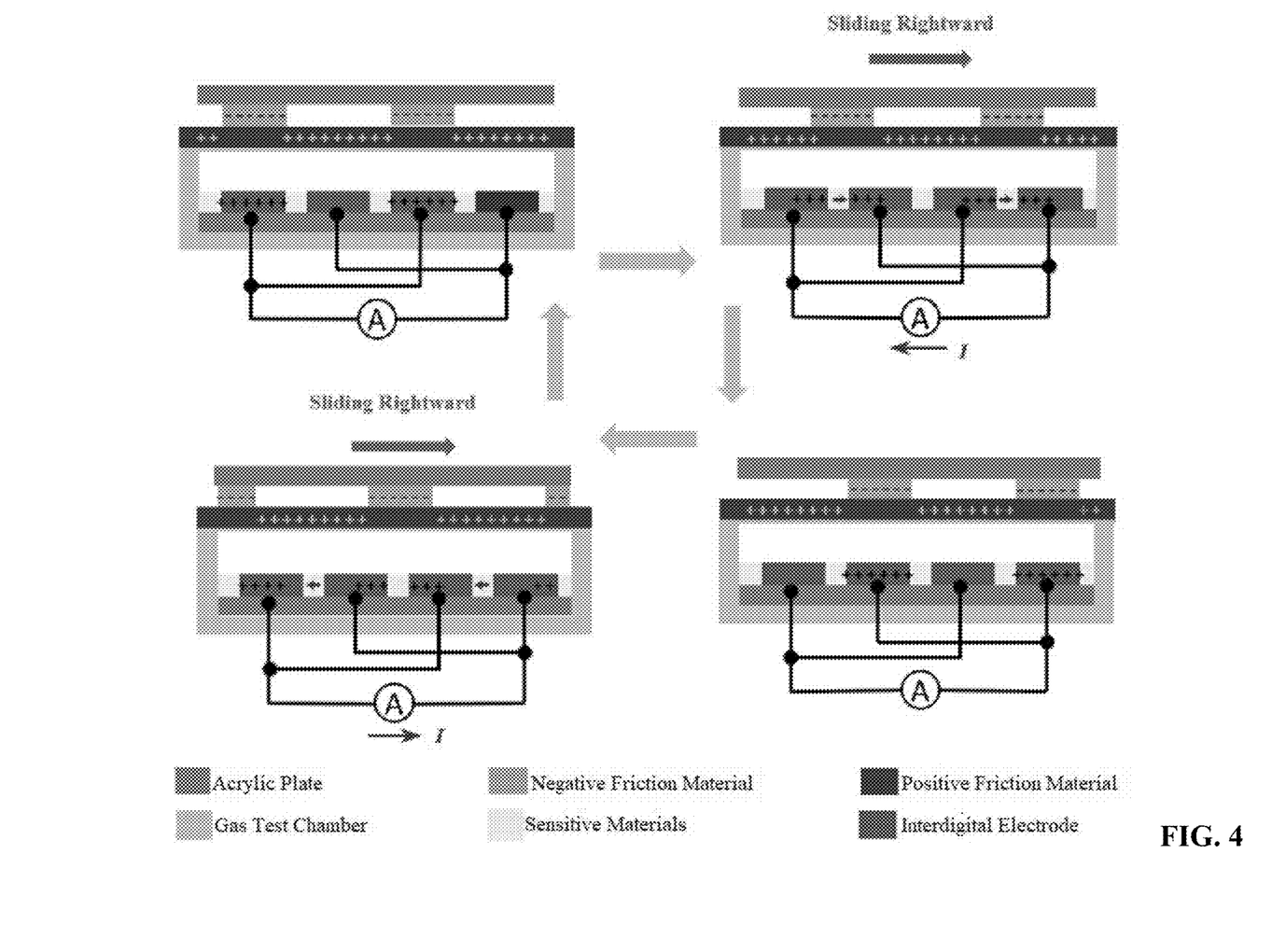

Example 1 is a wireless self-powered gas sensor based on electromagnetic oscillations triggered by external forces. The first friction layer 1 is selected from PTFE material and the second friction layer 2 is selected from Nylon material are employed as the energy harvesting component. Under the external force, the first friction layer sliding away from the original position. Due to the principle of contact electrification, polarized charges of equal opposite signs are formed on PTFE and Nylon, and time-varying electromagnetic oscillation energy (displacement current) is delivering to external space. The interdigital electrode comprises a first comb electrode and a second comb electrode, in which the two comb electrodes are arranged crosswise. FIG. 3 shows the conductive electricity mechanism of the sensor in Example 1 when the first friction layer slides to the left. Initially, the position of PTFE's grating solid portion overlaps the position of the first comb electrode. Since PTFE own higher triboelectric negativity than Nylon, triboelectric charges occur between the two surfaces, resulting in the induction of positive charge on the first comb electrode, which corresponds to the negative charge on the surface of PTFE. In this state, there is no charge between the first comb electrode and the second comb electrode due to electrostatic equilibrium. When the first friction layer (PTFE) starts to slide to the left, the position of the grating solid part of the friction layer gradually moves away from the overlapping position of the first comb electrode to the overlapping position of the second comb electrode. In this process, a potential difference is generated and electrons from the second comb electrode are transferred to the first comb electrode due to the electrostatic induction, generating a transient current in the external load. When the position of the solid portion of the PTFE grating is fully aligned with the position of the second comb electrode, all positive charges are transferred to the second comb electrode, achieving new electrostatic equilibrium. This is an interdigital move step. When the position of the solid part of the PTFE grating continues to move to the left to overlap with the position of the first comb electrode, the positive charge will be attracted back to the first comb electrode by static electricity, generating a reverse current in the circuit. Thus, a whole electricity generation cycle is completed. When the first friction layer slides in the direction indicated by the arrow in the figure, the opposite process occurs, as shown in FIG. 4.

Figure 5:
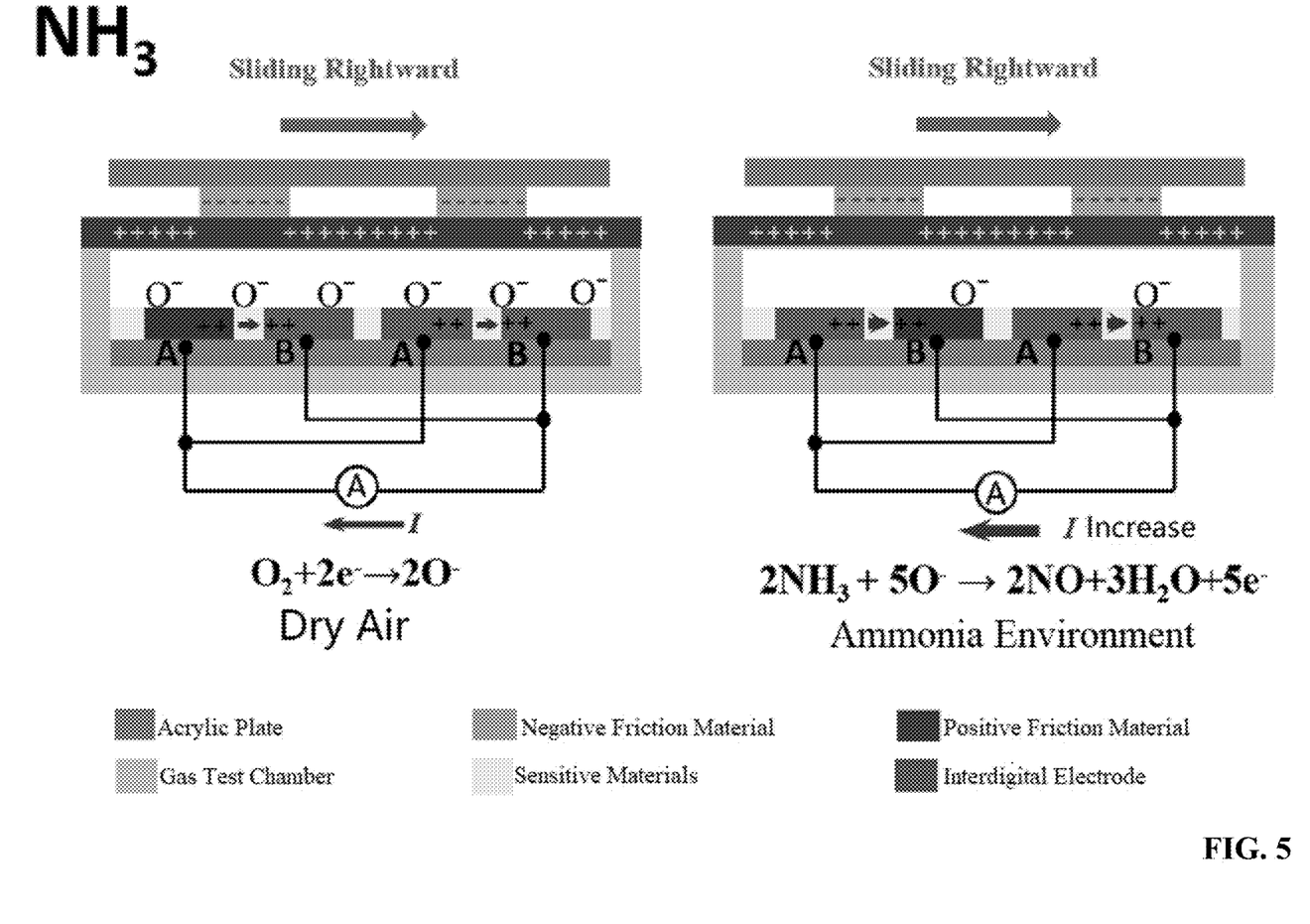
FIG. 5 explains the gas-sensitive mechanism of the wireless self-powered gas sensor based on electromagnetic oscillations triggered by external forces in the ammonia environment provided in Example 1.

FIG. 5 shows the gas-sensitive mechanism of the wireless self-powered gas sensor based on electromagnetic oscillations triggered by external forces in the ammonia environment mentioned in Example 1. The external mechanical energy is converted into time-varying electromagnetic oscillation energy through the first and second friction layers, which is delivered to the interdigital electrode coated with polyaniline (PANT) gas-sensitive material. Since the size of the sensor and the moving speed of the first friction layer are constant, the potential difference generated by the two ends of the interdigital finger electrode remains unchanged. The carrier concentration in gas sensitive materials will vary with the gas adsorption-desorption process. Therefore, the external mechanical motion modulates the chemical-specific reaction process on the surface of gas-sensitive structure into the output signal to realize the self-driven detection of the type and concentration of the measured gas. When the sensor is exposed to dry air, oxygen molecules absorb free electrons from the gas-sensitive membrane to form oxygen ions. This process reduces the electron concentration in the gas-sensitive film and thus the induced current. Subsequently, $NH_3$ as a reducing gas will provide electrons to the gas-sensitive film, increasing the carrier concentration of the gas-sensitive film and thus the induced current.

EXAMPLE 2

In this implementation, the gas-sensitive material is changed to zinc oxide in comparison with Example 1. The process of Step 3 is: adding 10 mg of zinc oxide to 10 mL of ethanol and stirring at room temperature for 2 h to fully disperse the zinc oxide and obtaining 1 mg/ml zinc oxide solution. The substrate with interdigital electrode was attached with PE film, exposing only the gap between the interdigital electrodes. The zinc oxide solution was uniformly coated in the gaps between interdigital electrodes by spinning coating method. Then, PE film was removed, and zinc oxide gas-sensitive material was deposited in the gap between the interdigital electrode. The remaining steps are the same as in Example 1, to obtain a sensor for detecting nitrogen dioxide in the exhaust of the vehicle.

Figure 6:
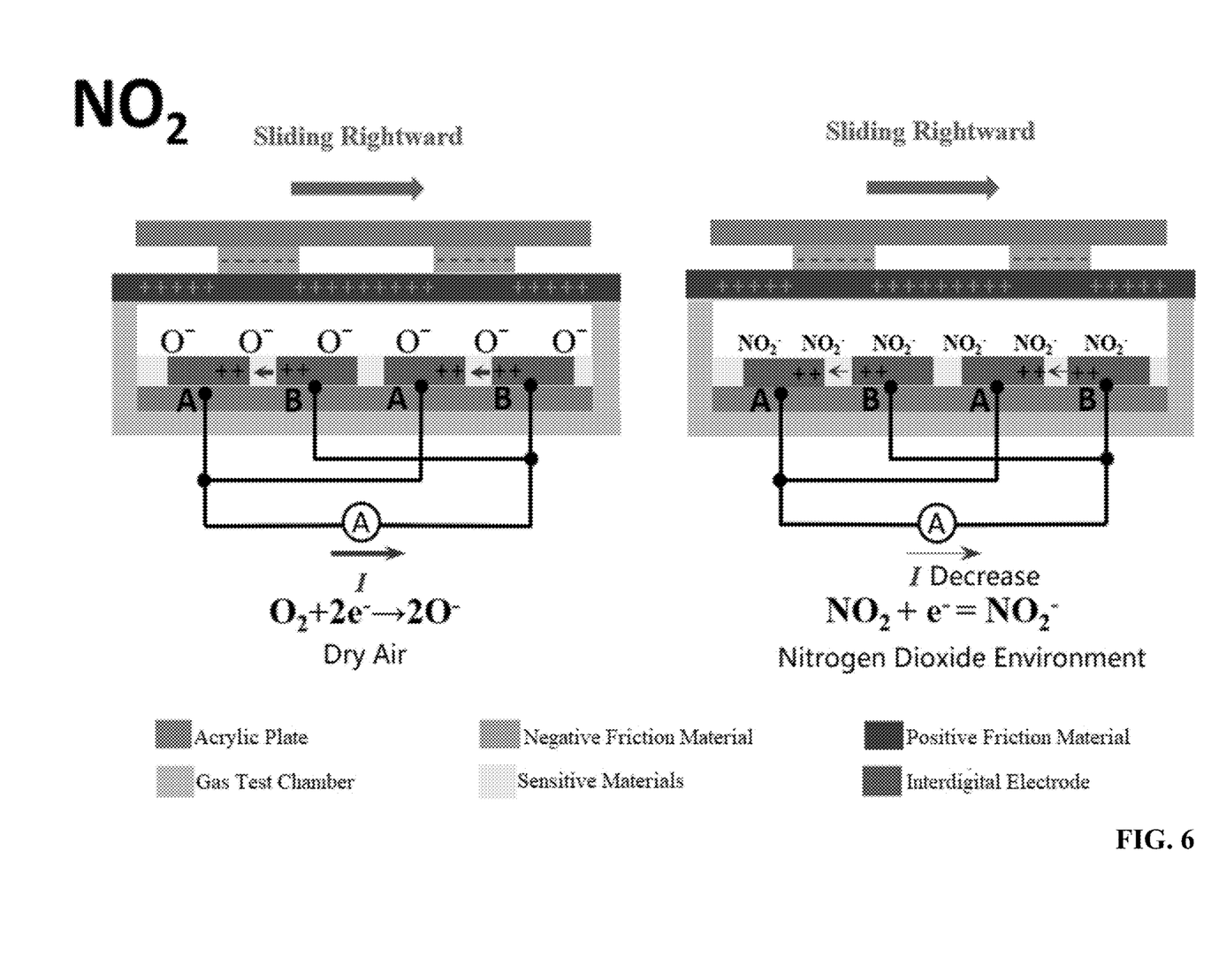
FIG. 6 demonstrates the gas-sensitive mechanism of the wireless self-powered gas sensor based on electromagnetic oscillations triggered by external forces in the nitrogen dioxide environment provided in Example 2.

FIG. 6 elucidates the gas-sensitive mechanism of the wireless self-powered gas sensor based on electromagnetic oscillations triggered by external forces in the nitrogen dioxide environment provided in Example 2. When the sensor is exposed to dry air, oxygen molecules absorb free electrons from the gas-sensitive film to form oxygen ions, the process that reduces the electron concentration of the gas-sensitive film and thus the induced current. Subsequently, $NO_2$ will further capture the electrons of gas-sensitive film, and reduce the electron concentration of gas-sensitive film, degrading the induced current. Therefore, with the difference of target gas concentration, the output current of the sensor will change, where the concentration of the target gas can be deduced by detecting the output electrical parameters of the sensor.

Figure 7:
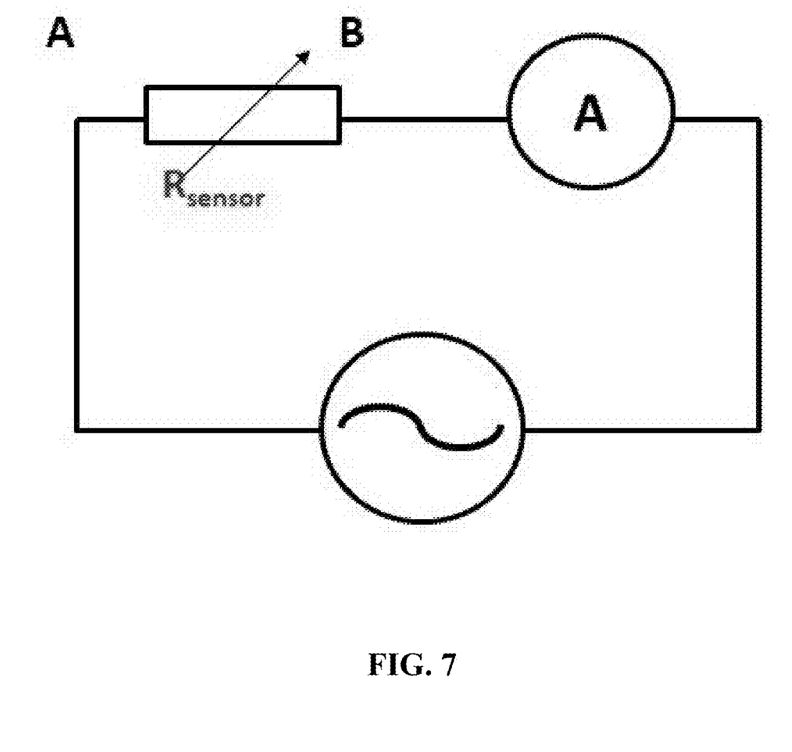
FIG. 7 shows the equivalent circuit diagram of the wireless self-powered gas sensor based on electromagnetic oscillations triggered by external forces.

FIG. 7 is the equivalent circuit diagram of the wireless self-powered gas sensor based on electromagnetic oscillations triggered by external forces. The energy harvesting component comprises the first friction layer and the second friction layer. The first friction layer has the same cross section size as the gas test chamber and is a grating structure. The second friction layer completely covers the outer surface of the gas test chamber, and the structure is equivalent to the generator powered by the gas-sensitive structure. The gas-sensitive film deposited in the interdigital electrode gap is equivalent to a gas sensitive resistance. By measuring the output current of the gas sensitive resistance, the concentration of the gas to be measured in the environment can be derived.

EXAMPLE 3

Figure 2:
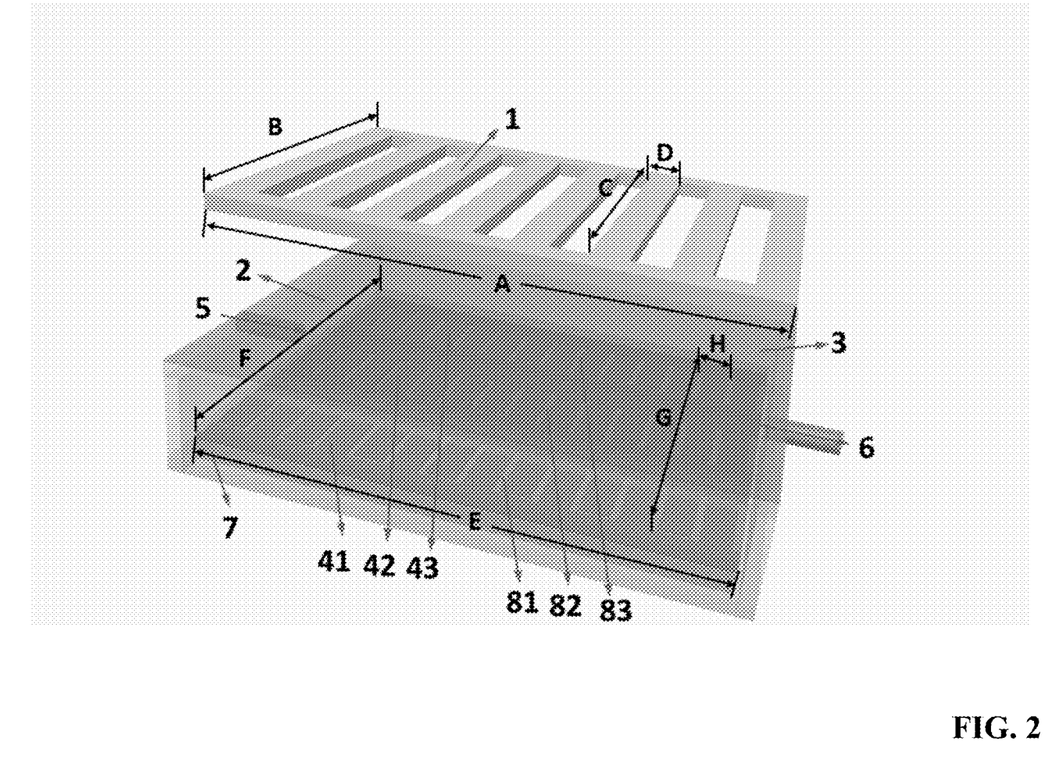
FIG. 2 illustrates the structure diagram of the wireless self-powered gas sensor array based on electromagnetic oscillations triggered by external forces.

The difference between this Example 3 and Example 1 is as follows: Three parallel interdigital electrodes are set at the bottom of the gas test chamber to build up the gas sensing array for simultaneously detecting two kind of gases, as shown in FIG. 2. The structure of the two IDE electrodes is exactly the same, and the length is equal to the length of the whole interdigital electrode. In the first row of interdigital electrode, the gas-sensitive material filled between adjacent electrodes was polyaniline, and the preparation process was the same as that in Example 1. In the second row of interdigital electrodes, the gas-sensitive material filled between adjacent electrodes is zinc oxide, and the preparation process is the same as in Example 2. The detection of ammonia gas is realized by detecting the electrical signal output at both ends of the first row of interdigital electrodes. The detection of nitrogen dioxide is realized by detecting the electrical signal output at both ends of the second interdigital electrode. Therefore, by constructing multiple rows of interdigital electrodes as the sensor array, the detection of multiple gases can be realized at the same time, which greatly improves the detection efficiency of gases.

It will be obvious to those skilled in the art that changes and modifications may be made, and therefore, the aim in the appended claims is to cover all such changes and modifications.

What is claimed is:

1. A device, comprising:
    an energy harvesting component; and
    a gas sensing component;
   wherein
    the gas sensing component comprises a gas test chamber, an interdigital electrode comprising gaps, and an acrylic substrate; the gas test chamber comprises an air inlet on one side and an air outlet on the other side; the interdigital electrode is disposed on the acrylic substrate and the acrylic substrate is disposed on a bottom of the gas test chamber; the gaps between the adjacent interdigital electrode are filled with a gas-sensitive material; two ends of the interdigital electrode are respectively connected to a first lead wire and a second lead wire; and
    the energy harvesting component comprises a first friction layer and a second friction layer; the second friction layer is disposed above the first friction layer and aligned with an outer surface of the gas test chamber; the first friction layer and the second friction layer have the same cross-sectional area as the gas test chamber; the first friction layer is a grating structure and comprises a negative friction material; the second friction layer comprises a positive friction material; and the grating structure is parallel to, and has identical characteristic parameters as, the electrode of interdigital electrodes.

2. The device of claim 1, wherein the solid part of the grating structure in the first friction layer has the same width as the interdigital electrode.

3. The device of claim 1, wherein the grating structure in the first friction layer is parallel to the electrode in the interdigital electrode and the following characteristic parameters are identical for these two configurations; the length of the grating structure is A, the width of the whole grating structure is B, the width of the transmittance part of the grating structure is C in the longitudinal direction, the width of the solid part of the grating structure is D in the transverse direction, with a duty ratio of 0.5; the length of the entire interdigital electrode is E, the width of the entire interdigital electrode is F, the longest distance between the two adjacent interdigital electrodes is G in the direction of the width of the interdigital electrode, and the crosswise width of each comb electrode in the fork finger electrode is H. A=E, B=F, C=G, D=H.

4. The device of claim 1, wherein the gas-sensitive material is an organic polymer, or a metal oxide, or an inorganic material that is sensitive to the target gas.

5. The device of claim 1, wherein the gas-sensitive material is composed of one or more materials selected from polyaniline, polyvinyl oxide, polyimide, sodium polystyrene sulfonate, polyimide, chitosan, and graphene oxide.

6. The device of claim 1, wherein the first friction layer is a first polymer film, and the second friction layer is a second polymer film; and the first polymer film has a stronger electron affinity than the second polymer film and thus the ability to attract electrons from the second polymer film.

7. The device of claim 1, wherein the first friction layer is selected from teflon, polyfluoroethylene, polyvinyl chloride or polyimide with a thickness of 10-50 μm; and the second friction layer is made of nylon, polyurethane or magnesium fluoride and has a thickness of 10-50 μm.

8. A method for preparation of the device of claim 1, the method comprising:
    1) cleaning and drying two pieces of polymer films;
    2) cutting a first polymer film into grating structure by laser as a first polymer film; cutting a second piece into a rectangular structure as a second polymer film; wherein the first polymer film and the second polymer film are utilized together as triboelectric materials; and an electron affinity of the first polymer film is stronger than that of the second polymer film;
    3) preparing the interdigital electrode through spin coating, spray coating, drop coating, sol gel, self-assembly or chemical vapor deposition; developing a gas-sensitive structure by depositing the gas-sensitive material between adjacent electrodes of the interdigital electrode in combination with a lift-off process;
    4) using a laser cutting machine to cut a plexiglass plate and assembling the gas test chamber; attaching the second polymer film to the outer surface of a top of the gas test chamber as the second friction layer; placing the first polymer film above the second polymer film as the first friction layer, wherein both sides of the gas test chamber are integrated air inlet and air outlet; and placing the gas-sensitive structure at the bottom of the gas test chamber to form a self-driven gas sensor; and
    5) connecting the two ends of the interdigital electrode to a test port of a current measuring instrument through a lead.

* * * * *